US00PP11555P

United States Patent [19]

Leis et al.

[11] Patent Number: Plant 11,555

[45] Date of Patent: Oct. 10, 2000

[54] STRAWBERRY PLANT NAMED 'CIVERO'

[75] Inventors: Michelangelo Leis; Dario Musacchi; Alessio Martinelli, all of Ferrara, Italy

[73] Assignee: C.I.V. Consorzio Italiano Vivaisti, Ferrara, Italy

[21] Appl. No.: 09/103,714

[22] Filed: Jun. 23, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 7,171 2/1990 Johnson, Jr. et al. ..... Plt./208
P.P. 9,130 5/1995 Sjulin et al. ..... Plt./208

*Primary Examiner*—Howard J. Locker
*Assistant Examiner*—Wendy A. Baker
*Attorney, Agent, or Firm*—Christie, Parker & Hale, LLP

[57] ABSTRACT

A new strawberry variety producing firm fruit on an early flowering plant.

3 Drawing Sheets

BACKGROUND OF THE INVENTION

The new variety of strawberry was created in a breeding program by crossing as male parent the variety known as 'Selva' (U.S. Plant Pat. No. 5266) and as female parent the variety known as 'Chandler' (U.S. Plant Pat. No. 5262).

The resulting seedling of the new variety was grown and asexually propagated by runners(stolons) in Ferrara, Italy. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Civero'. Among the characteristics which distinguish the new variety from other varieties are a combination of traits which include firm fruit having strong aroma and very good taste. 'Civero' is particularly suited for culture in low chilling areas, both under plastic and outdoors. It is not an ever bearing variety. Bud break is about January 15–25 in Battipaglia, Italy, and first bloom occurs in the early part of February and lasts about ten days.

COMPARISON TO CLOSEST VARIETY

The new variety is closest to the variety 'Chandler' (U.S. Plant Pat. No. 5262), but is distinguished therefrom by the following characteristics possessed by 'Civero' which are different than, or not possessed by, 'Chandler': 'Civero' flowers earlier than 'Chandler' and the fruit has a lighter color. The varieties also differ in fruit shape. The following table provides a comparison of the varieties 'Civero', 'Chandler' and 'Selva', as well as additional descriptive information for 'Civero'.

TABLE 1

| Character | 'Civero' | 'Chandler' | 'Selva' |
|---|---|---|---|
| Leaf color (upper surface) RHS | 139A | 139A | 141A |
| Terminal leaflet length mean (cm) | 6.9 | 6.85 | 7.1 |
| Terminal leaflet width mean (cm) | 6.21 | 6.23 | 6.38 |
| Terminal leaflet ratio (L/W) | 1.11 | 1.10 | 1.11 |
| Petiole length mean (cm) | 18.77 | 14.69 | 14.92 |
| Petiole width mean (mm) | 2.9 | 3.5 | 3.1 |
| Petiole pubescence | medium-low | medium | medium |

TABLE 1-continued

| Character | 'Civero' | 'Chandler' | 'Selva' |
|---|---|---|---|
| Petiole pose of hairs | slightly upwards | slightly upwards | outwards |
| Petiole color (RHS) | 145B | 149B | 149A |

The above characteristics have been determined in Battipaglia, (Salerno) Southern Italy in the month of April.

The leaves of 'Civero' are medium in size. The terminal leaflet is slightly longer than wide as described by the length/width ratio. Serrations at the margins are medium, between 3.0 and 4.5 mm deep. Single and double serrations are present on the leaf, with moderately obtuse apexes. Petioles are long and medium big in diameter, with medium-low pubescence. Hairs grow slightly upwards on the petiole. Stipules are in pairs and are green in color with weak pigmentation.

BRIEF DESCRIPTION OF ILLUSTRATIONS

The accompanying photographs show typical specimens of the new variety, including fruit, foliage and flower, in color as nearly true as it is reasonably possible to make in color illustrations of this character.

DESCRIPTION OF THE NEW VARIETY

Figure 1:
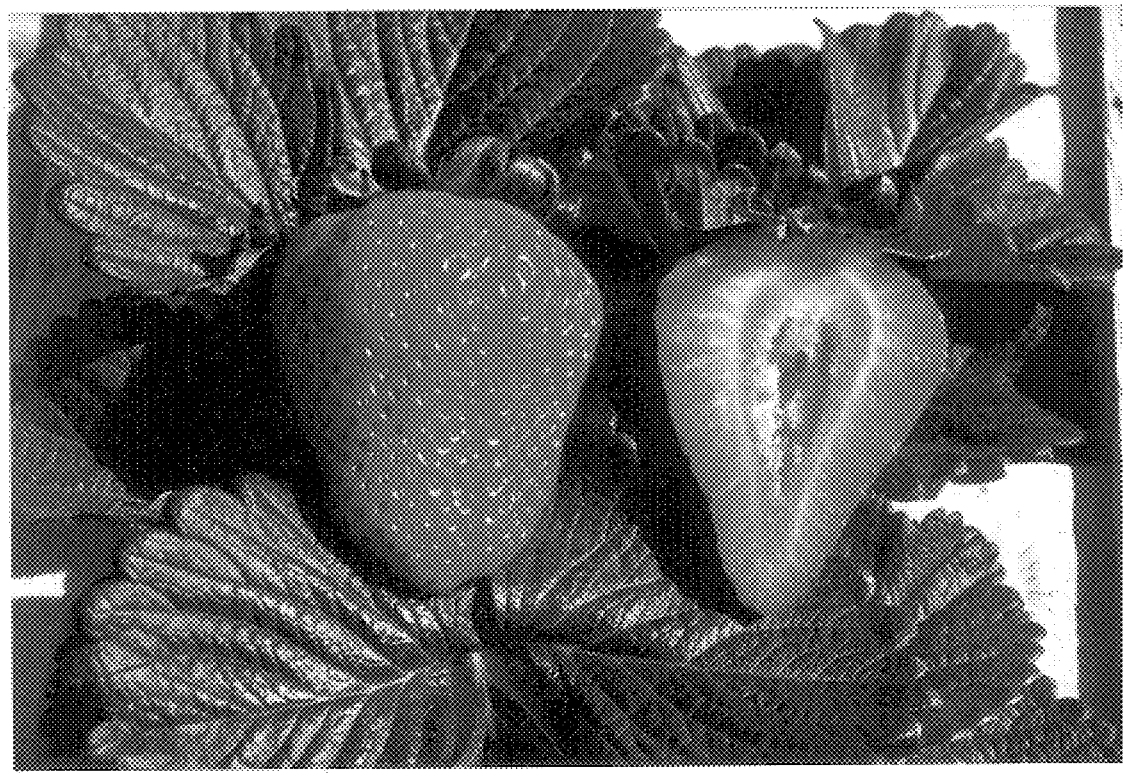
FIG. 1 shows typical fruit in cross section illustrating the typical flesh and flesh coloration, conspicuous core and core cavity and shape.
Figure 2:
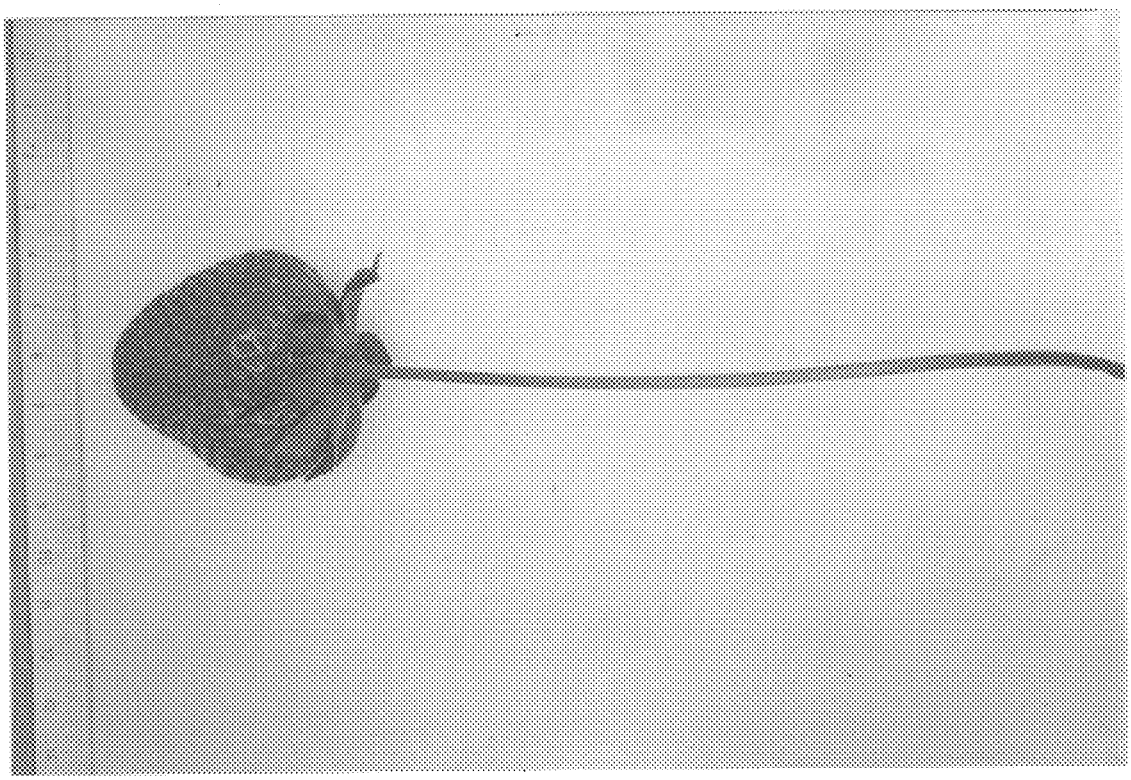
FIG. 2 shows a whole strawberry attached to its petiole.
Figure 3:
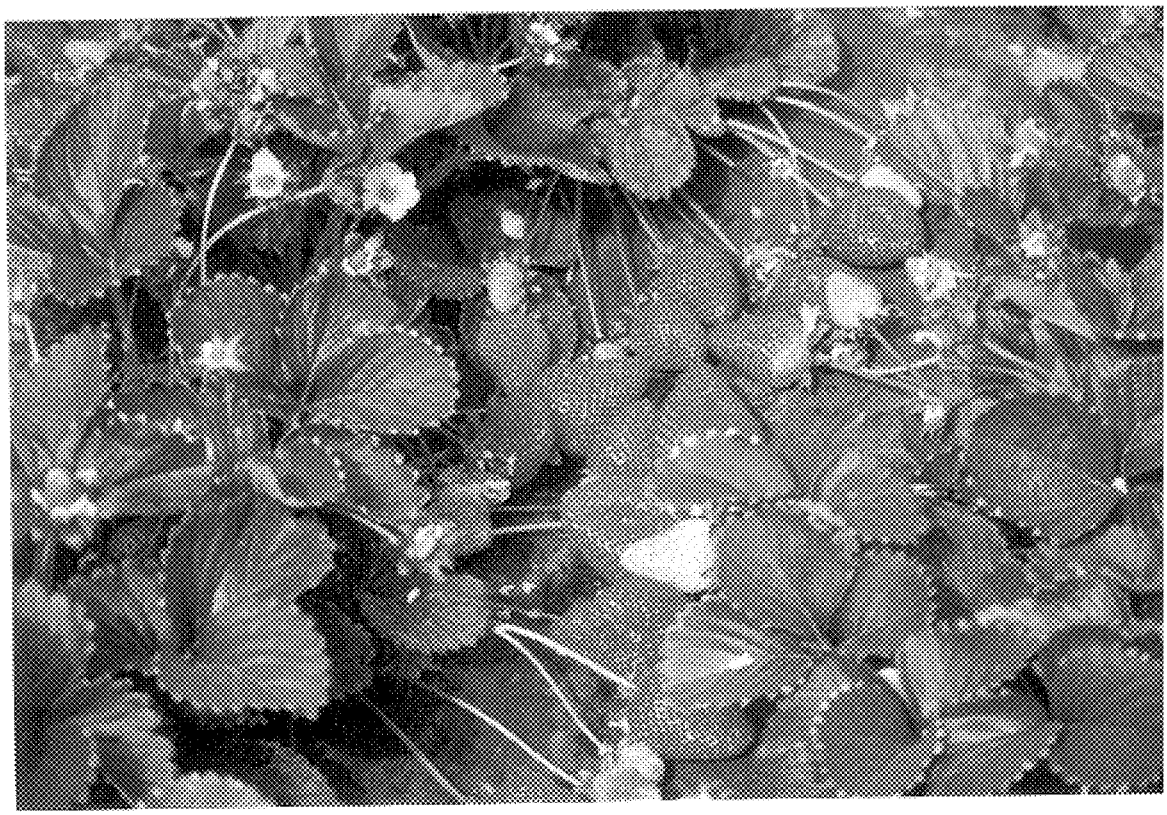
FIGS. 3 and 4 show the fruit on the plant.
Figure 4:
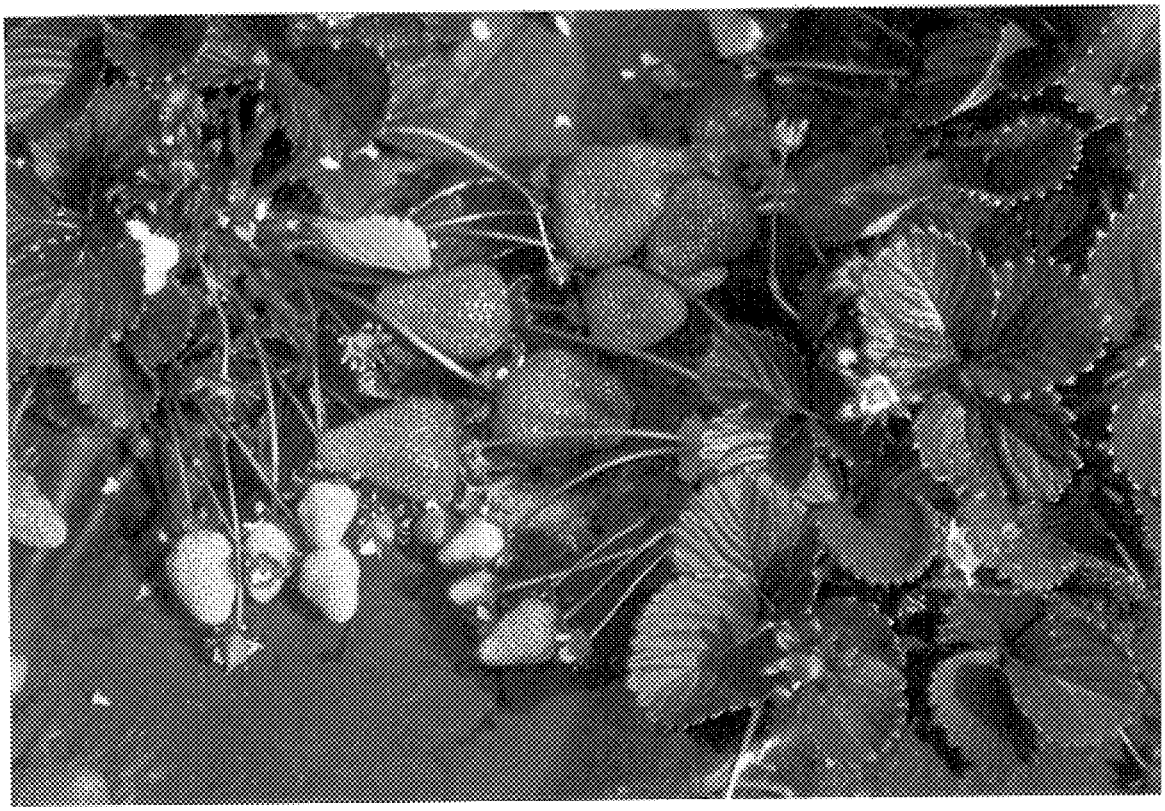
Figure 5:
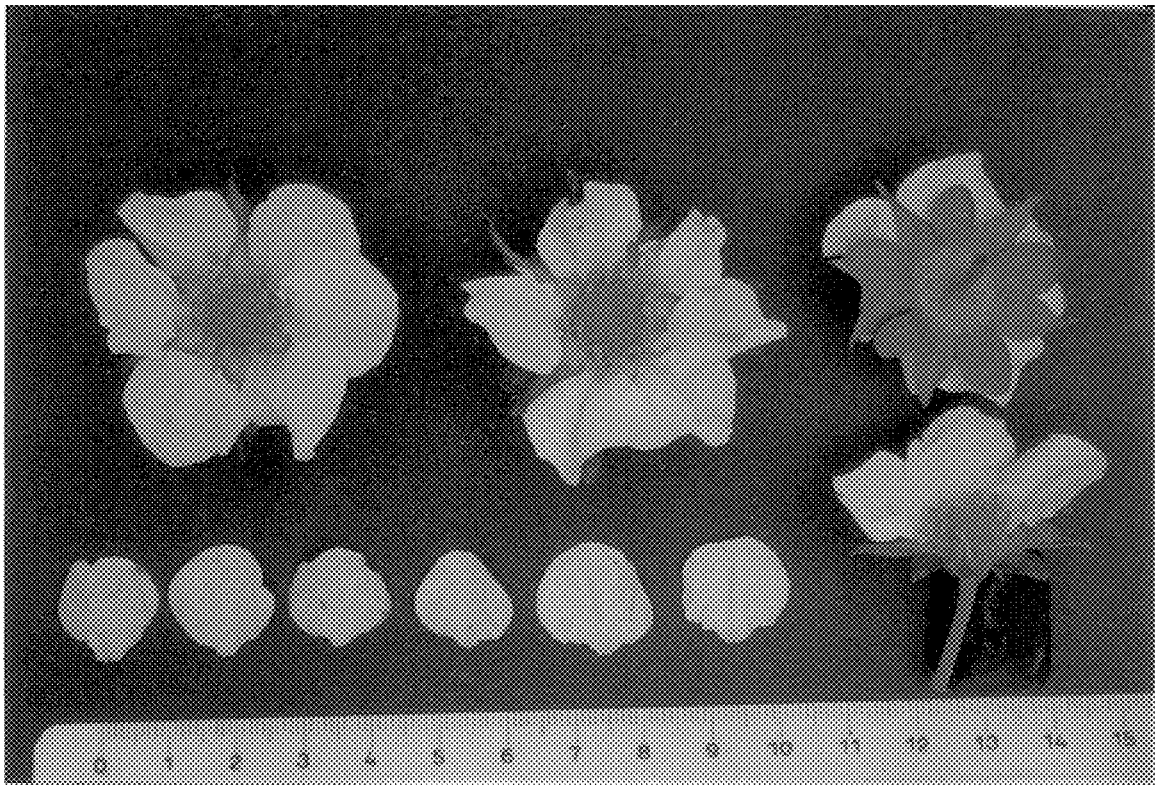
FIG. 5 shows the flower and reproductive organs of the new variety.
Figure 6:
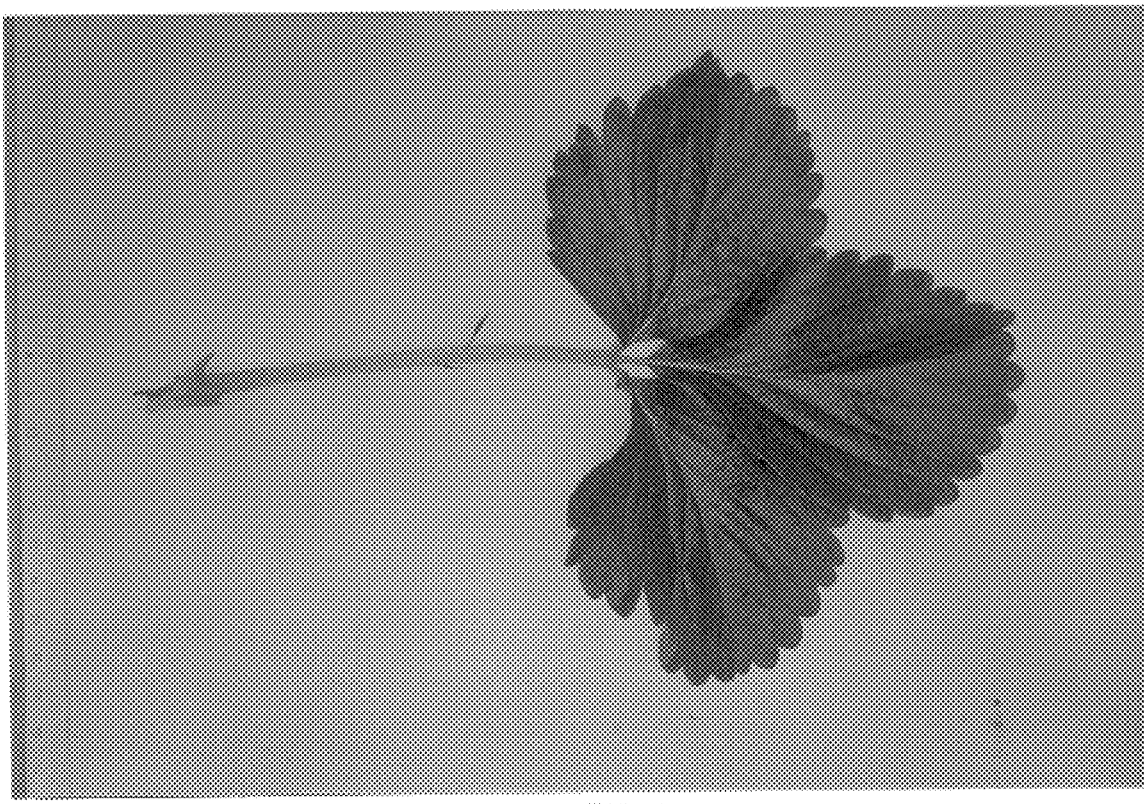
FIG. 6 shows the upper surface of a typical foliage of the new variety.

The following detailed description of the new variety is based upon observations taken of plants and fruits grown "underglass," in Naples, Italy, in the month of April.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPAGATION

The new variety is principally propagated by way of runners (stolons). Although propagation by runners is presently preferred, other known methods of propagating strawberry plants, such as micropropagation, may be used. The new variety roots well after transplanting.

The term "blistering" used herein refers to the texture or rugosity inherent to leaves and is generally a constant characteristic.

VARIETY

'Civero':Breeder Reference 92.H1.51

Classification:*Fragaria, L.*

General:

*Preferred planting time.*—September in Naples, Italy.

*Regional or climatic growing preferences.*—Warm climates under plastic or in open field.

*Petioles, size and length.*—Medium size and length outwards hairs, weak pigmentation of stipules.

*Runners.*—Abundant, of medium thickness, weak pigmentation and weak pubescence.

Plant:

*Habit.*—Globose.

*Size.*—About 20 to 28 cm in diameter.

*Leaves.*—Shape: As long as broad, shape of base is acute, cross section is concave Color: Top surface near 139A, undersurface near 139C Leaflet number: 3 Texture: Medium blistering Serration: Obtuse Inflorescence:

*Size and shape.*—Medium size at the same level of foliage blooms with 2 to inflorescences, each bearing about 8 to 10 flowers.

*Pedicel.*—Flowers appear single as the division between primary and secondary terms is close to the bud

*Abundance.*—Abundant.

*Color.*—White, petals overlap and are as long as broad.

*Anthers and pollen.*—Abundant pollen, very quick pollination. Color: Yellow.

*Calyx size, sepal form and color.*—Same size of the corolla, inner calyx is of the same size of the outer calyx, size of sepals is medium with elongated shape.

Flower

*Diameter.*—About 33–36 mm.

*Inflorescence.*—Mean length about 22.8 cm, about 8 to 10 flowers for each inflorescence

*Petals.*—Flowers normally have about 6 petals, each petal about as long as wide, length about 12.2 mm, width about 12.4 mm; ratio length/width is about 0.98; color near 155D to 155C

*Sepals.*—About 10, elongated and normally detached from the fruit

*Calyx.*—About 29–31 mm

Fruit:

*Size and shape.*—Big, truncated-conical, prevalent shape, no significant differences between primary and secondary fruits; main fruit width measured across the widest part of the berry is about 4.4 cm; the main fruit length is about 5.3 cm; the color of the achenes is near 153C.

*Seed characteristics.*—Achenes are inserted below surface and are present over all the fruit.

*Juiciness.*—Medium.

*Taste.*—Very good, sweet, low acidity.

*Flesh color.*—Near 40C.

*Exterior surface.*—Color: Near 45B Glossiness: Strong Shape: Truncated conical Firmness: Very strong Characteristics of flesh and core Flesh is very firm, aromatic; medium red near 45A color; with little cavity. Aroma: Very strong. Keeping qualities: Keeps taste and color very well.

TABLE 2

| 1998 | Soluble solids | Acidity | Flavor | Firmness |
|---|---|---|---|---|
| 'Civero' | 7.57 | 6.17 | 4.35 | 4.07 |
| 'Chandler' | 6.61 | 9.32 | 3.57 | 3.23 |

Soluble solids are expressed in Brix degrees. Acidity in g/l of citric acid, taste and firmness are rated 1 to 5, with 1 being minimum and 5 being maximun. Six tests were done during the harvest season. Fruit Yield Information: Mean market fruit yield and fruit size of 'Civero' in comparison with that of 'Chandler' are reported in Table 3. The data (referring to the years 1996, 1997 and 1998) are taken from plants harvested from late March through the first week of June in Battipaglia, (Salerno) Southern Italy. The production plants were cold stored plants planted in the first week of September of the year before fruit harvest.

TABLE 3

| Mean 1996-97-98 | Market fruit yield | Av. fruit size grams |
|---|---|---|
| 'Civero' | 540 | 16.25 |
| 'Chandler' | 635 | 16.88 |

The unit of measurement of market fruit yield is grams per plant; Following are the dates of first pick, last pick and peak of production of the variety 'Civero' in comparison with the reference variety 'Chanlder' in the years 1996, 1997 and 1998 (in the zone of Battipaglia, Southern, Italy):

| | Civero | Chandler |
|---|---|---|
| Year 1996 | | |
| First pick | April 5 | April 12 |
| Last pick | June 4 | June 4 |
| Production peak | May 9 | May 2 |
| Year 1997 | | |
| First pick | March 19 | March 21 |
| Last pick | May 30 | June 3 |
| Production peak | April 18 | April 20 |
| Year 1998 | | |
| First pick | March 27 | March 27 |
| Last pick | May 18 | May 14 |
| Production peak | April 7 | April 15 |

Disease resistance: Medium susceptibility to the principal root diseases of strawberry and mildew.

Winter or frost resistance: Not suited for high chilling areas.

Chilling: Fruit of 'Civero' are advantageously cooled at about 0° C. immediately after harvest, and kept in cold storage for about 2 days. Shelf life at room temperature after that treatment is about 3–5 days.

We claim:

1. A new and distinct strawberry plant of the variety substantially as shown and described.

* * * * *